United States Patent [19]

George et al.

[11] Patent Number: 5,550,125
[45] Date of Patent: Aug. 27, 1996

[54] 3-(2-AMINOMETHYL)-4-[3-TRIFLUOROMETHYL)BENZOYL]-3-4 DIHYDRO-2H-1,4-BENZOXAZINE DERIVATIVES AND THEIR THERAPEUTIC APPLICATION

[75] Inventors: Pascal George, St Arnoult en Yvelines; Jonathan Frost, Wissous; Patrick Pasau, Bagneux; Corinne Rousselle; Régine Bartsch, both of Fontenay aux Roses; Paul Howard Williams, Paris; Jean Claude Muller, Morsang sur Orge, all of France

[73] Assignee: Synthelabo, Le Plessis Robinson, France

[21] Appl. No.: 382,589

[22] Filed: Feb. 2, 1995

[30] Foreign Application Priority Data

Feb. 3, 1994 [FR] France .................................. 94 01196
Feb. 3, 1994 [FR] France .................................. 94 01197

[51] Int. Cl.⁶ ...................... A61K 31/535; C07D 413/06; C07D 471/04; C07D 495/04
[52] U.S. Cl. ........................................ 514/230.5; 544/105
[58] Field of Search ........................... 544/105; 514/230.5

[56] References Cited

U.S. PATENT DOCUMENTS

| | | | |
|---|---|---|---|
| 4,636,563 | 1/1987 | Abou-Gharbia | 546/87 |
| 4,977,159 | 12/1990 | Sevrin et al. | 514/292 |
| 5,447,928 | 9/1995 | Williams | 514/213 |

FOREIGN PATENT DOCUMENTS

| | | | |
|---|---|---|---|
| 2117122 | 9/1994 | Canada | C07D 265/36 |
| 0614893 | 9/1994 | European Pat. Off. | |
| 1287584 | 1/1969 | Germany | |

OTHER PUBLICATIONS

Cannon, Joseph G. et al, "Conformationally Restricted Congeners of Dopamine Derived from 2–Aminoindan", J. Med. Chem., 1982, vol. 25, pp. 1442–1446.

*Primary Examiner*—Philip I. Datlow
*Attorney, Agent, or Firm*—Jacobson, Price, Holman & Stern, PLLC

[57] ABSTRACT

Compounds of the general formula (I)

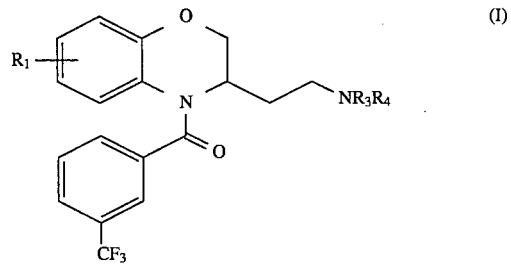

wherein $R_1$ represents a hydrogen, fluorine or chlorine atom or a methyl, $C_1$–$C_3$ alkoxy or nitro group; $R_3$ represents a hydrogen atom or a $C_1$–$C_3$ alkyl group; $R_4$ represents a 2,3-dihydro-1H-inden-2-yl, 2,3-dihydro-1H-inden-1-yl or 1,2,3,4-tetrahydronaphthalen-1-yl group; or alternatively $R_3$ and $R_4$ complete, with the nitrogen atom to which they are attached, a 1,2,3,4-tetrahydro-9H-pyrido[3,4-b]indol-2-yl, 1,2,3,4-tetrahydro-9H-pyrido[4,3-b]indol-3-yl, 4,5,6,7-tetrahydrothieno[2,3-c]pyrid-6-yl, 4,5,6,7-tetrahydrothieno[3,2-c]pyrid-6-yl or 2,3-dihydro-1H-isoindol-2-yl group; are useful for the treatment and prevention of cerebral disorders.

3 Claims, No Drawings

3-(2-AMINOMETHYL)-4-[3-TRIFLUOROMETHYL)BENZOYL]-3-4 DIHYDRO-2H-1,4-BENZOXAZINE DERIVATIVES AND THEIR THERAPEUTIC APPLICATION

The present invention provides to 3-(2-aminoethyl)-4-[3-(trifluoromethyl)benzoyl]-3,4-dihydro-2H-1,4-benzoxazine derivatives, their preparation and their therapeutic application.

According to the invention there are provided compounds of the general formula

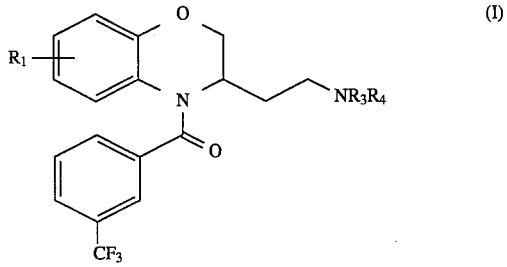

wherein $R_1$ represents a hydrogen, fluorine or chlorine atom or a methyl, $C_1$–$C_3$ alkoxy or nitro group;

$R_3$ represents a hydrogen atom or a $C_1$–$C_3$ alkyl group;

$R_4$ represents a 2,3-dihydro-1H-inden-2-yl group, a 2,3-dihydro-1H-inden-1-yl group or a 1,2,3,4tetrahydronaphthalen-1-yl group;

or alternatively $R_3$ and $R_4$ together complete, with the nitrogen atom to which they are attached a 1,2,3,4-tetrahydro-9H-pyrido[3,4-b]indol-2-yl group, a 1,2,3,4-tetrahydro-9H-pyrido[4,3-b]indol-3-yl group, a 4,5,6,7-tetrahydrothieno[2,3-c]pyrid-6-yl group, a 4,5,6,7-tetrahydrothieno[3,2-c]pyrid-6-yl group or a 2,3-dihydro-1H-isoindol-2-yl group, the respective formulae of which are as follows:

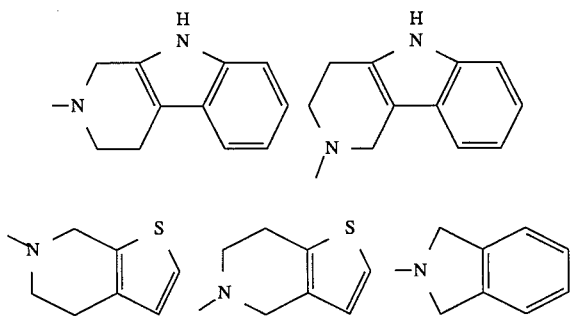

The preferred compounds are those in whose formula $R_1$ represents a fluorine or chlorine atom or a methyl or methoxy group, $R_3$ represents a hydrogen atom or a $C_1$–$C_3$ alkyl group and $R_4$ represents a 2,3-dihydro-1H-inden-2-yl group, a 2,3-dihydro-1H-inden-1-yl group or a 1,2,3,4-tetrahydronaphthalen-1-yl group.

Since the molecule represented by the general formula (I) possesses an asymmetric carbon atom (at position 3 of the benzoxazine ring system), the compounds of the invention may exist in the form of pure enantiomers or of a mixture of enantiomers. Furthermore, when $R_4$ represents a 2,3-dihydro-1H-inden- 1-yl group or a 1,2,3,4-tetrahydronaphthalen-1-yl group, the molecule contains a second asymmetric centre.

A compound according to the invention may thus exist in the form of a pure optical isomer or a mixture of such isomers.

The compounds of the invention may be provided in the form of free bases or of addition salts with acids.

According to the invention, the compounds of general formula (I) may be prepared by a process illustrated by the following scheme:

A 2-aminophenol of general formula (II), in which $R_1$ is as defined above, is reacted with trifluoroacetic anhydride, of formula (III), in the presence of a base such as pyridine, in a solvent such as ether.

An amide of general formula (IV) is obtained, which is reacted with ethyl 4-bromo-2-butenoate, of formula (V), in the presence of a base such as sodium ethoxide, in a solvent such as ethanol, at a temperature of the order of 80° C. The ester function of the ethyl 3,4-dihydro-2H-1,4-benzoxazine-3-acetate derivative, of general formula (VI), is then reduced. A reducing agent such as lithium aluminium hydride is generally used, except when $R_1$ represents a nitro group when sodium borohydride in 1,1-dimethylethanol, according to *Synth. Commun.* (1982) 12(6) 463, is used. The product which is 3,4-dihydro-2H-1,4-benzoxazine-3-ethanol derivative of general formula (VII), is reacted, in a solvent such as dichloromethane, with 3-(trifluoromethyl)benzoyl chloride, of formula (VIII), in order to obtain an alcohol of general formula (IX), which is reacted with thionyl chloride in order to obtain a compound of general formula (X). Finally, the compound of general formula (X) is reacted with an amine of general formula $HNR_3R_4$ in which $R_3$ and $R_4$ are as defined above.

Scheme

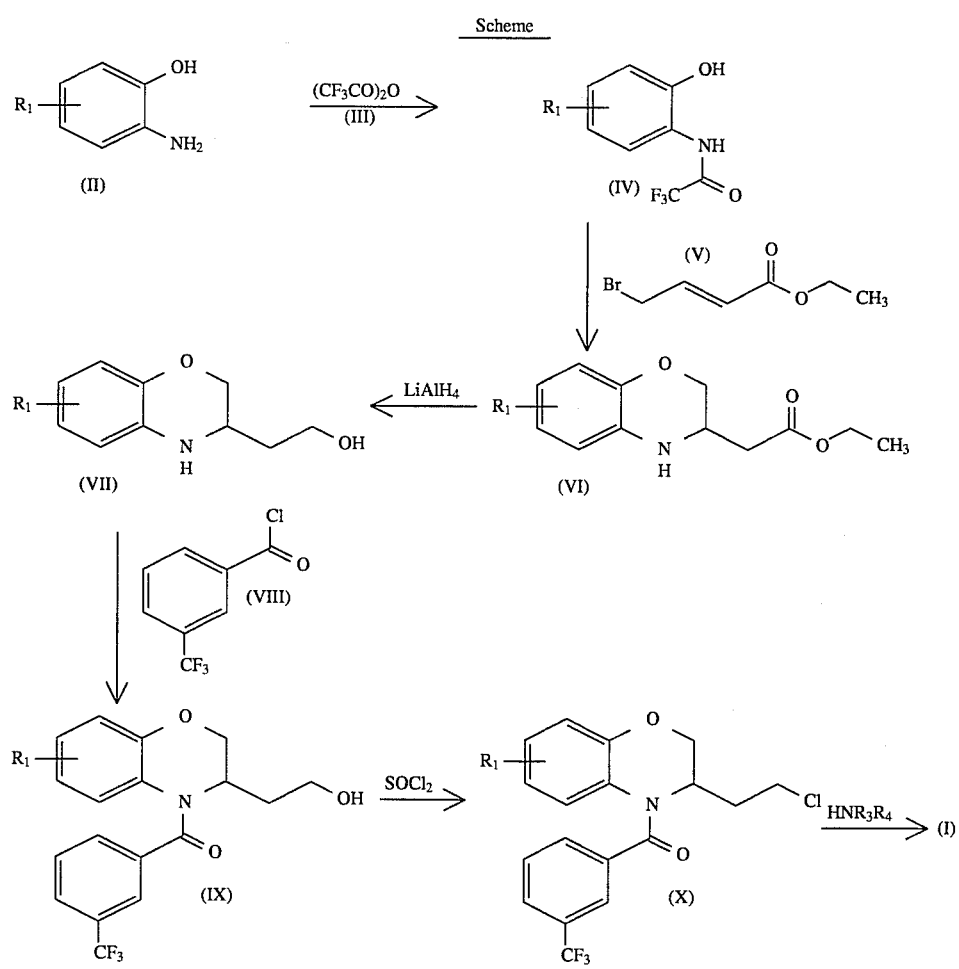

The starting materials are commercially available or are described in the literature, or may be synthesized according to methods which are described therein or which are known to those skilled in the art.

In particular, the aminophenol of general formula (II) in which $R_1$ represents a methoxy group is described in *J. Amer. Chem. Soc.* (1949) 71 1265.

The amines of formula $HNR_3R_4$ in which $R_4$ represents a 2,3-dihydro-1H-inden-2-yl group are described in *J. Med. Chem.* (1980) 23 745.

The amines of formula $HNR_3R_4$ in which $R_4$ represents a 2,3-dihydro-1H-inden-1-yl group are described in *J. Amer. Chem. Soc.* (1966) 88 2233.

The amines of formula $HNR_3R_4$ in which $R_4$ represents a 1,2,3,4-tetrahydronaphthalen-1-yl group are described in *J. Amer. Chem. Soc.* (1960) 82 459, *C. R. Hebd. Séances Acad. Sci. Ser. C.* (1969) 268 2225 and *J. Med. Chem.* (1966) 9 830.

1,2,3,4-Tetrahydro-9H-pyrido[3,4-b]indole is described in *Organic Synthesis* (1971) 51 136.

1,2,3,4-Tetrahydro-9H-pyrido[4,3-b]indole is described in *J. Chem. Soc. (C)* (1968) 1235.

4,5,6,7-Tetrahydrothieno[2,3-c]pyridine and 4,5,6,7-tetrahydrothieno[3,2-c]pyridine are described in *Arkiv. Kemi* (1970) 13(19) 217.

4,5,6,7-Tetrahydrothieno[3,2-c]pyridine is also described in Patent Application EP-0,342,118.

2,3-Dihydro-1H-isoindole is described in *Organic Synthesis Coll.* (1973) 5 406 and 1064.

If it is desired to obtain an optically pure compound of general formula (I), it is possible to use an optically pure alcohol of general formula (IX), which may be prepared, for example, via an enzymatic method.

The basic principle of this enzymatic method consists in separating an optically pure alcohol and the corresponding acetate, of opposite configuration, for example by chromatography on a column of silica gel.

According to a first variant, the racemic alcohol of formula (IX) is subjected to a chemical acylation, for example using acetic anhydride, one of the two enantiomers of the racemic acetate is hydrolysed stereospecifically in the presence of an enzyme, and the acetate which has not been hydrolysed is separated out. This gives an optically pure alcohol and an optically pure acetate of opposite configuration which may itself, if so desired, be hydrolysed via a chemical or enzymatic route to give the second enantiomer of the alcohol.

According to a second variant, the racemic alcohol of formula (IX) is subjected to a stereospecific acylation in the presence of an enzyme which catalyses the esterification of only one of the enantiomers, for example using vinyl acetate. As before, this gives an optically pure alcohol and an optically pure acetate of opposite configuration which may itself, if so desired, be hydrolysed via a chemical or enzymatic route to give the second enantiomer of the alcohol.

Depending on the enzyme used, the laevorotatory or dextrorotatory enantiomer of the alcohol (IX) and its acetate of opposite configuration may be obtained in the two variants.

The enzymes which may be used are, for example, the lipases of Mucor Miehei, of Penicillium cyclopium or of wheat germ.

Moreover, when $R_4$ represents a 2,3-dihydro-1H-inden-1-yl group or a 1,2,3,4-tetrahydronaphthalen-1-yl group, the compounds contain, in their molecule, a second asymmetric centre and thus exist in the form of diastereoisomers. The use of chiral amines (*J. Amer. Chem. Soc.* (1966) 88 2233 and *C. R. Hebd. Séances Acad. Sci. Ser. C.* (1969) 268 2225) allows the synthesis of optically pure compounds.

The examples which will follow illustrate in detail the preparation of a few compounds according to the invention.

The elemental microanalyses and the I.R. and N.M.R. spectra confirm the structures of the compounds obtained. The numbers indicated in parentheses in the titles of the examples correspond to those in the table given later.

EXAMPLE 1

(Compound No. 1)

(±)-3-[2-(1,2,3,4-Tetrahydro-9H-pyrido[3,4-b]indol-2 -yl)ethyl]-4-[(3-trifluoromethyl)benzoyl]-3,4-dihydro-2H-1,4-benzoxazine (E)-2-butenedioate (1:1).

1.1. N-(2-Hydroxyphenyl)trifluoroacetamide.

A suspension of 1.5 l of diethyl ether and 104 g (0.95 mol) of 2-aminophenol is prepared in a 4 l reactor, with magnetic stirring, and 77 ml of pyridine are added. The reaction medium is cooled with a mixture of ice and ethanol, 200 g (0.95 mol) of trifluoroacetic anhydride are added dropwise over 1 h, the mixture is allowed to return to room temperature and stirring is continued for 1 h.

Ice-water is added and the organic phase is separated out, washed successively with 1N hydrochloric acid, with water, with saturated sodium hydrogen carbonate solution and with saturated sodium chloride solution. It is dried over magnesium sulphate and the solvent is evaporated off.

170 g of product are obtained, which product is used as it is in the following step.

1.2. Ethyl (±)-3,4-dihydro-2H-1,4-benzoxazine-3-acetate.

650 ml of ethanol are introduced into a 3 l reactor, with magnetic stirring, cooled to 0° C., 5.9 g (0.259 mol) of sodium are added slowly, in small portions, followed by successive dropwise addition of 53 g (0.259 mol) of N-(2-hydroxyphenyl)trifluoroacetamide and 50 g (0.259 mol) of 75% pure ethyl 4 -bromo-2-butenoate, and the mixture is heated at 80° C. for 1.5 h.

The solvent is evaporated off and the residue is taken up in 160 ml of water and 65 ml of 1N sodium hydroxide and is extracted with diethyl ether. The organic phase is washed with saturated sodium chloride solution and dried over magnesium sulphate, and the solvent is evaporated off. 38.22 g of product are obtained, which product is purified by chromatography on a column of silica gel, eluting with a mixture of cyclohexane and isopropyl ether (in a ratio of 1/1).

28.02 g of product are obtained.

1.3. (±)-3,4-Dihydro-2H-1,4-benzoxazine-3-ethanol.

190 ml of tetrahydrofuran are introduced into a 1 l reactor, cooled with a mixture of ice and salt and, under an argon atmosphere, 7.7 g (0.202 mol) of lithium aluminium hydride are added, followed by dropwise addition of 28.02 g (0.127 mol) of ethyl (±)-3,4-dihydro-2H-1,4-benzoxazine-3-acetate dissolved in 190 ml of tetrahydrofuran, and the mixture is stirred for 3 h.

The reactor is cooled with a mixture of cardice and acetone, 60 ml of water and 30 ml of 1N sodium hydroxide are added dropwise and stirring is continued for 0.5 h.

The precipitate is removed by filtration on kieselgel, it is rinsed successively with tetrahydrofuran and ethyl acetate, the filtrate solvents are evaporated off and 24.99 g of crude product are obtained, which product is purified by chromatography on a column of silica gel, eluting with a mixture of cyclohexane and ethyl acetate (in a ratio of 1/1).

15.5 g of product are obtained.

1.4. (±)-4-[3-(Trifluoromethyl)benzoyl]-3,4-dihydro-2H-1,4-benzoxazine-3-ethanol.

77 ml of dichloromethane# 15.93 g (0.072 mol) of (±)-3,4-dihydro-2H-1,4-benzoxazine-3-ethanol and 10.67 g (0.077 mol) of potassium carbonate are introduced into a 500 ml round-bottomed flask, 16.05 g (0.077 mol) of 3-(trifluoromethyl)benzoyl chloride dissolved in 77 ml of dichloromethane are added dropwise and the mixture is stirred at room temperature for 3.5 h.

72 ml of 1N sodium hydroxide are added and the organic phase is separated out and washed with water and then with saturated sodium chloride solution and dried over magnesium sulphate, and the solvent is evaporated off. 33.48 g of oily product are obtained, which product is purified by chromatography on a column of silica gel, eluting with a mixture of cyclohexane and ethyl acetate (in a ratio of 1/1).

21.93 g of product are obtained.

1.5. (±)-3-(2-Chloroethyl)-4-[3-(trifluoromethyl) benzoyl]-3,4-dihydro-2H-1,4-benzoxazine.

To 21.93 g of (±)-4-[3-(trifluoromethyl)benzoyl]-3,4-dihydro-2H-1,4-benzoxazine-3-ethanol dissolved in 280 ml of dichloromethane are added 18 ml (0.248 mol) of thionyl chloride and the mixture is stirred at room temperature for 6 h.

The solvent is evaporated off and the residue is taken up in toluene, which is evaporated off, and the oil obtained is purified by chromatography on a column of silica gel, eluting with a mixture of cyclohexane and isopropyl ether (in a ratio of 1/1).

21.74 g of product are obtained.

1.6. (±)-3-[2-(1,2,3,4-Tetrahydro-9H-pyrido[3, 4-b]indol-2-yl)ethyl]-4-[(3-trifluoromethyl) benzoyl]-3,4-dihydro-2H-1,4-benzoxazine (E)-2-butenedioate (1:1).

To a solution of 2.5 g (0.007 mol) of (±)-3-2-chloroethyl)-4-[3-(trifluoromethyl)benzoyl]-3,4 -dihydro-2H-1,4-benzoxazine in 20 ml of N,N-dimethylformamide at room temperature, under an argon atmosphere and with magnetic stirring, are added 1.20 g (0.007 mol) of 1,2,3,4-tetrahydro-9H-pyrido[3,4-b]indole, 1.45 g (0.0105 mol) of potassium carbonate and 1.16 g (0.007 mol) of potassium iodide, and the mixture is heated at 160° C. for 1 h. It is cooled, 80 ml of water and 80 ml of ethyl acetate are added, the phases are separated and the aqueous phase is extracted with twice 80 ml of ethyl acetate. The organic phases are combined and are washed with 100 ml of saturated sodium chloride solution, dried over magnesium sulphate and filtered, and the solvent is evaporated off. 4 g of oily product are obtained, which product is purified by chromatography on a column of silica gel, eluting with a mixture of cyclohexane and ethyl acetate (in a ratio of 7/3).

3.5 g of pure base are obtained in the form of a yellow oil.

The fumarate is prepared by adding one equivalent of fumaric acid, and it is isolated and recrystallized, in the form of white crystals, from ethanol.

1.71 g of fumarate are finally isolated. Melting point: 211°–212° C.

EXAMPLE 2

(Compound No. 12)

(±)-6-Fluoro-3-[2-(4,5,6,7-tetrahydrothieno[2,3-c]pyrid-6-yl)ethyl]-4-[(3-trifluoromethyl)benzoyl]-3,4-dihydro-2H-1,4-benzoxazine (E)-2-butenedioate (1:1).

2.1. 2-Amino-4-fluorophenol.

To a solution of 50 g (0.318 mol) of 4-fluoro-2-nitrophenol in 1.5 l of water, with magnetic stirring, are added 120 g (0.689 mol) of sodium hydrosulphite, the mixture is heated to reflux, 120 g (0.689 mol) of sodium hydrosulphite are added and heating is continued at reflux for 0.75 h.

The mixture is cooled, sodium hydrogen carbonate is added portionwise until the pH becomes basic, 1 l of diethyl ether is added, the phases are separated and the aqueous phase is extracted with 1 l of diethyl ether. The organic phases are combined and washed with 1 l of water and 1 l of saturated sodium chloride solution, dried over magnesium sulphate and filtered, and the solvent is evaporated off. 21.1 g of product are obtained, which product is used as it is in the following step.

2.2. N-(5-Fluoro-2-hydroxyphenyl)trifluoroacetamide.

A suspension of 260 ml of diethyl ether and 21 g (0.165 mol) of 2-amino-4-fluorophenol is prepared in a 1 l reactor, with magnetic stirring, 14 ml of pyridine are added and the reaction medium is cooled with a mixture of ice and ethanol. 23.3 ml (0.165 mol) of trifluoroacetic anhydride are added dropwise over 1 h, the mixture is allowed to return to room temperature and stirring is continued for 3 h.

Ice-water is added and the organic phase is separated out and washed successively with 170 ml of 1N hydrochloric acid, with water, with saturated sodium hydrogen carbonate solution and with saturated sodium chloride solution. It is dried over magnesium sulphate and the solvent is evaporated off.

32.7 g of product are obtained, which product is used as it is in the following step.

2.3. Ethyl (±)-6-fluoro-3,4-dihydro-2H-1,4-benzoxazine-3-acetate.

370 ml of ethanol are introduced into a 1 l reactor, with magnetic stirring, cooled to 0° C., and 3.5 g (0.146 mol) of sodium are introduced slowly, in small portions, followed by successive dropwise addition of 32.54 g (0.146 mol) of N-(5-fluoro-2-hydroxyphenyl)trifluoroacetamide and 28.18 g (0.146 mol) of 75% pure ethyl 4-bromo-2-butenoate, and the mixture is heated at 80° C. for 3 h.

The solvent is evaporated off and the residue is taken up in 90 ml of water and 37 ml of 1N sodium hydroxide and is extracted with diethyl ether. The organic phase is washed with saturated sodium chloride solution and dried over magnesium sulphate, and the solvent is evaporated off. 38.74 g of product are obtained, which product is purified by chromatography on a column of silica gel, eluting with a mixture of cyclohexane and isopropyl ether (in a ratio of 1/1).

23.22 g of product are obtained.

2.4. (±)-6-Fluoro-3,4-dihydro-2H-1,4-benzoxazine-3-ethanol.

145 ml of tetrahydrofuran are introduced into a 1 l reactor which is cooled with a mixture of ice and salt, and, under an argon atmosphere, 5.9 g (0.153 mol) of lithium aluminium hydride are added, followed by dropwise addition of 23.22 g (0.097 mol) of ethyl (±)-6-fluoro-3,4-dihydro-2H-1,4-benzoxazine-3-acetate dissolved in 145 ml of tetrahydrofuran, and the mixture is stirred for 2.5 h. The reactor is cooled with a mixture of cardice and acetone, 45 ml of water and 23 ml of 1N sodium hydroxide are added dropwise and stirring is continued for 0.5 h.

The precipitate is removed by filtration on kieselgel and is rinsed successively with tetrahydrofuran and ethyl acetate, the filtrate solvents are evaporated off and 18.07 g of crude product are obtained, which product is purified by chromatography on a column of silica gel, eluting with a mixture of cyclohexane and ethyl acetate (in a ratio of 1/1).

13.9 g of product are obtained.

2.5. (±)-6-Fluoro-4-[3-(trifluoromethyl)benzoyl]-3,4-dihydro-2H-1,4-bensoxazine-3-ethanol.

70 ml of dichloromethane, 13.69 g (0.069 mol) of (±)-6-fluoro-3,4-dihydro-2H-1,4-benzoxazine-3-ethanol and 10.27 g (0.074 mol) of potassium carbonate are introduced into a 500 ml round-bottomed flask, 15.44 g (0.074 mol) of 3-(trifluoromethyl)benzoyl chloride dissolved in 70 ml of dichloromethane are added dropwise and the mixture is stirred at room temperature for 5 h.

70 ml of 1N sodium hydroxide are added and the organic phase is separated out and washed with water and then with saturated sodium chloride solution and dried over magnesium sulphate, and the solvent is evaporated off. 27.53 g of oily product are obtained, which product is purified by chromatography on a column of silica gel, eluting with a mixture of cyclohexane and ethyl acetate (in a ratio of 2/1).

11.27 g of product are obtained.

2.6. (±)-3-(2-Chloroethyl)-6-fluoro-4-[3-(trifluoromethyl)benzoyl]-3,4-dihydro-2H-1,4-benzoxazine.

To 11.27 g (0.031 mol) of (±)-6-fluoro-4-[3-(trifluoromethyl)benzoyl]-3,4-dihydro-2H- 1,4-benzoxazine-3-ethanol dissolved in 140 ml of dichloromethane are added 9 ml (0.124 mol) of thionyl chloride and the mixture is stirred at room temperature for 5 h.

The solvent is evaporated off and the residue is taken up in toluene, which is evaporated off, and the oil obtained is purified by chromatography on a column of silica gel, eluting with a mixture of cyclohexane and isopropyl ether (in a ratio of 1/1).

10.33 g of product are obtained.

2.7. (±)-6-Fluoro-3-[2-(4,5,6,7-tetrahydrothieno [2,3-c]pyrid-6-yl)ethyl]-4-[(3-trifluoromethyl) benzoyl]-3,4-dihydro-2H-1,4-benzoxazine (E)-2-butenedioate (1:1).

To a solution of 1.11 g (0.003 mol) of (±)-3-( 2-chloroethyl)-6-fluoro-4-[3-(trifluoromethyl)benzoyl]-3,4-dihydro-2H-1,4-benzoxazine in 15 ml of N,N-dimethylformamide, at room temperature, under argon and with magnetic stirring, are added 0.66 g (0.003 mol) of 4,5,6,7-tetrahydrothieno[2,3-c]pyridine oxalate, 1.19 g (0.0086 mol) of potassium carbonate and 0.5 g (0.003 mol) of potassium iodide, and the mixture is heated at 160° C. for 1 h. It is cooled, 50 ml of water and 50 ml of diethyl ether are added, the phases are separated and the aqueous phase is extracted with twice 50 ml of diethyl ether. The organic phases are combined and washed with 50 ml of saturated sodium chloride solution, dried over magnesium sulphate and filtered, and the solvent is evaporated off. 1.56 g of oily product are obtained, which product is purified by chromatography on a column of silica gel, eluting with a mixture of cyclohexane and ethyl acetate (in a ratio of 7/3).

0.80 g of base is obtained in the form of a yellow oil.

The fumarate is prepared by adding one equivalent of fumaric acid, and it is isolated and recrystallized, in the form of white crystals, from 2-propanol.

0.77 g of fumarate is finally isolated. Melting point: 181°–182° C.

EXAMPLE 3

(Compound No. 24)

(±)-3-[2-[(2,3-Dihydro-1H-inden-2-yl) methylamino]ethyl]-6-methoxy-4-[3-(trifluoromethyl)benzoyl]-3,4-dihydro-2H-1,4-benzoxazine ethanedioate (1:1).

3.1. N-(2-Hydroxy-5-methoxyphenyl)trifluoroacetamide.

A suspension of 1 l of diethyl ether and 75.33 g (0.54 mol) of 2-amino-4-methoxyphenol is prepared in a 2 l reactor, with magnetic stirring, and 56 ml of pyridine are added. The reaction medium is cooled with a mixture of ice and ethanol, 131.4 g (0.625 mol) of trifluoroacetic anhydride are added dropwise over 1 h, the mixture is allowed to return to room temperature and stirring is continued for 2 h.

Ice-water is added and the organic phase is separated out and washed successively with 500 ml of 1N hydrochloric acid, with water, with saturated sodium hydrogen carbonate solution and with saturated sodium chloride solution. It is dried over magnesium sulphate and the solvent is evaporated off.

41.6 g of product are obtained, which product is used as it is in the following step.

3.2. Ethyl (±)-6-methoxy-3,4-dihydro-2H-1, 4-benzoxazine-3-acetate.

450 ml of ethanol are introduced into a 1 l reactor, with magnetic stirring, cooled to 0° C., and 7 g (0.32 mol) of sodium are added slowly, in small portions, followed by successive dropwise addition of 37.94 g (0.16 mol) of N-(2-hydroxy-5-methoxyphenyl)trifluoroacetamide and 41.2 g (0.16 mol) of pure ethyl 4-bromo-2-butenoate, and the mixture is heated at 80° C. for 2 h.

The solvent is evaporated off and the residue is taken up in 100 ml of water and 40 ml of 1N sodium hydroxide and is extracted with diethyl ether. The organic phase is washed with saturated sodium chloride solution and dried over magnesium sulphate, and the solvent is evaporated off. 38.46 g of product are obtained, which product is purified by chromatography on a column of silica gel, eluting with a mixture of cyclohexane and isopropyl ether (in a ratio of 1/1).

21.22 g of product are obtained.

3.3. (±)-6-Methoxy-3,4-dihydro-2H-1,4-benzoxazine-3-ethanol.

130 ml of tetrahydrofuran are introduced into a 1 l reactor which is cooled with a mixture of ice and salt and, under an argon atmosphere, 5 g (0.132 mol) of lithium aluminium hydride are added, followed by dropwise addition of 20.73 g (0.0825 mol) of ethyl (±)-6-methoxy-3,4-dihydro-2H-1,4-benzoxazine-3-acetate dissolved in 130 ml of tetrahydrofuran, and the mixture is stirred for 1.5 h. The reactor is cooled with a mixture of cardice and acetone, 40 ml of water and 20 ml of 1N sodium hydroxide are added dropwise and stirring is continued for 0.5 h.

The precipitate is removed by filtration on kieselgel and is rinsed successively with tetrahydrofuran and ethyl acetate, the filtrate solvents are evaporated off and 25.15 g of crude product are obtained, which product is purified by chromatography on a column of silica gel, eluting with a mixture of cyclohexane and ethyl acetate (in a ratio of 1/1).

10.53 g of product are obtained.

3.4. (±)-6-Methoxy-4-[3-(trifluoromethyl)benzoyl]-3,4-dihydro-2H-1,4-benzoxazine-3-ethanol.

80 ml of dichloromethane, 10.53 g (0.05 mol) of (±)-6-methoxy-3,4-dihydro-2H-1,4-benzoxazine-3-ethanol and 7.4 g (0.0535 mol) of potassium carbonate are introduced into a 500 ml round-bottomed flask and 11.16 g (0.0535 mol) of 3-(trifluoromethyl)benzoyl chloride dissolved in 80 ml of dichloromethane are added dropwise, and the mixture is stirred at room temperature for 2 h.

50 ml of 1N sodium hydroxide are added and the organic phase is separated out, washed with water and then with saturated sodium chloride solution and dried over magnesium sulphate, and the solvent is evaporated off. 22.25 g of oily product are obtained, which product is purified by chromatography on a column of silica gel, eluting with a mixture of cyclohexane and ethyl acetate (in a ratio of 2/1).

14.74 g of product are obtained.

3.5. (±)-3-(2-Chloroethyl)-6-methoxy-4-[3-(trifluoromethyl)benzoyl]-3,4-dihydro-2H-1,4-benzoxazine.

To 14.74 g (0.039 mol) of (±)-6-methoxy-4-[3-(trifluoromethyl)benzoyl]-3,4-dihydro-2H-1,4 -benzoxazine-3-ethanol dissolved in 165 ml of dichloromethane are added 14 ml (0.19 mol) of thionyl chloride and the mixture is stirred at room temperature for 5 h.

The solvent is evaporated off and the residue is taken up in toluene and evaporated to dryness, and the oil obtained is purified by chromatography on a column of silica gel, eluting with a mixture of cyclohexane and isopropyl ether (in a ratio of 1/1).

14.7 g of product are obtained.

3.6. (±)-3-[2-[(2,3-Dihydro-1H-inden-2-yl)methylamino] ethyl]-6-methoxy-4-[3-(trifluoromethyl) benzoyl]-3,4-dihydro-2H-1,4-benzoxazine ethanedioate (1:1).

To a solution of 1.6 g (0.004 mol) of (±)-3-(2-chloroethyl)-6-methoxy-4-[3 -(trifluoromethyl)benzoyl]-3,4-dihydro-2H-1,4-benzoxazine in 18 ml of N,N-dimethylformamide, at room temperature, under an argon atmosphere and with magnetic stirring, are added 0.73 g (0.004 mol) of N-methyl-2,3-dihydro-1H-inden-2-amine hydrochloride, 1.38 g (0.01 mol) of potassium carbonate and 0.66 g (0.004 mol) of potassium iodide, and the mixture is heated at 150° C. for 1 h.

It is cooled and 38 ml of water and 70 ml of diethyl ether are added, the phases are separated and the aqueous phase is extracted with twice 70 ml of diethyl ether. The organic phases are combined and washed with 70 ml of saturated sodium chloride solution, dried over magnesium sulphate and filtered, and the solvent is evaporated off. 1.91 g of oily product are obtained, which product is purified by chromatography on a column of silica gel, eluting with a mixture of dichloromethane and methanol (in a ratio of 85/15).

0.940 g of pure base is obtained in the form of a yellow oil. The oxalate is prepared by adding one equivalent of oxalic acid, and it is isolated and recrystallized, in the form of white crystals, from ethyl acetate.

0.370 g of oxalate is finally isolated. Melting point: 185°–187° C.

EXAMPLE 4

(Compound No. 30)

6-Chloro-3-[2-[(1,2,3,4-tetrahydronaphthalen-1-yl) methylamino]ethyl]-4-[3-(trifluoromethyl) benzoyl]-3,4-dihydro-2H-1,4-benzoxasine (E)-2-butenedioate (1:1), 65:35 mixture of (±)-diastereoisomers.

4.1. N-(5-Chloro-2-hydroxyphenyl)trifluoroacetamide.

25 g (0.174 mol) of 2-amino-4-chlorophenol are suspended in 320 ml of diethyl ether in a 1 litre reactor, with magnetic stirring, and 18 ml of pyridine are added. The medium is cooled with a mixture of ice and ethanol, 24.6 ml (0.174 mol) of trifluoroacetic anhydride are added dropwise over 1 hour, the mixture is allowed to return to room temperature and stirring is continued for 1 hour.

Ice-water is added, the phases are separated after settling has taken place and the organic phase is washed successively with 320 ml of 1N hydrochloric acid solution, with water, with saturated sodium hydrogen carbonate solution and then with saturated sodium chloride solution, dried over magnesium sulphate and the solvent is evaporated off. 40.3 g of product are obtained, which product is used as it is in the following step.

4.2. Ethyl (±)-6-chloro-3,4-dihydro-2H-1,4-benzoxazine-3-acetate.

420 ml of ethanol are introduced into a 3 litre reactor, with magnetic stirring, cooled to 0° C., and 3.8 g (0.166 mol) of sodium are added slowly, in small portions, followed by successive and dropwise addition of 40 g (0.166 mol) of N-(5-chloro-2-hydroxyphenyl)trifluoroacetamide and 40 g (0.155 mol) of 75% pure ethyl 4-bromo-2-butenoate, and the mixture is heated at 85° C. for 2 hours. The solvent is evaporated off and the residue is taken up in 100 ml of water and 40 ml of 1N sodium hydroxide and extracted with diethyl ether. The organic phase is separated out, washed with saturated aqueous sodium chloride solution, dried over magnesium sulphate and evaporated. 28.58 g of product are obtained, which product is purified by chromatography on a column of silica gel, eluting with a cyclohexane/isopropyl ether (1/1 ratio) mixture.

23.72 g of product are obtained.

4.3. (±)-6-Chloro-3,4-dihydro-2H-1,4-benzoxazine-3-ethanol.

150 ml of tetrahydrofuran are placed in a 1 litre reactor which is cooled with a mixture of ice and salt, and, under an argon atmosphere, 5.92 g (0.156 mol) of lithium aluminium hydride are added, followed by dropwise addition of 23.52 g (0.0973 mol) of ethyl (±)-6-chloro-3,4-dihydro-2H-1,4-benzoxazine-3-acetate dissolved in 150 ml of tetrahydrofuran, and the mixture is stirred for 1.5 hours. The reactor is cooled with a mixture of cardice and acetone, 40 ml of water and 20 ml of 1N sodium hydroxide are added dropwise and the mixture is stirred for 0.5 hour. The precipitate is filtered on kieselgel and rinsed with tetrahydrofuran and then with ethyl acetate, and the solvent is evaporated off. 27.5 g of crude product are isolated, which product is purified by chromatography on a column of silica gel, eluting with a cyclohexane/ethyl acetate (1/1 ratio) mixture.

19.67 g of product are obtained.

4.4. (±)-6-Chloro-4-[(3-trifluoromethyl)benzoyl]-3, 4-dihydro-2H-1,4-benzoxazine-3-ethanol.

100 ml of dichloromethane, 19.17 g (0.09 mol) of (±)-6-chloro-3,4-dihydro-2H-1,4-benzoxazine-3-ethanol and 13.3 g (0.096 mol) of potassium carbonate are introduced into a 1 litre round-bottomed flask and 20 g (0.096 mol) of 3-(trifluoromethyl)benzoyl chloride dissolved in 100 ml of dichloromethane are added dropwise, and the mixture is stirred at room temperature for 3 hours.

90 ml of 1N sodium hydroxide are added, the organic phase is separated out and washed with water and then with saturated sodium chloride solution, dried over magnesium sulphate and the solvent is evaporated off. 36 g of oily product are obtained, which product is purified by chromatography on a column of silica gel, eluting with a cyclohexane/ethyl acetate (2/1 ratio) mixture.

24.21 g of product are obtained.

4.5. (±)-6-Chloro-3-(2-chloroethyl)-4-[(3-trifluoromethyl) benzoyl]-3,4-dihydro-2H-1,4-benzoxazine.

To 24.21 g of (±)-6-chloro-4-[(3 -trifluoromethyl)benzoyl]-3,4-dihydro-2H-1,4 -benzoxazine-3-ethanol dissolved in 260 ml of dichloromethane are added 18 ml (0.25 mol) of thionyl chloride and the mixture is stirred at room temperature for 6 hours.

The solvent is evaporated off and the residue is taken up in toluene and evaporated. The 25.21 g of oil obtained are purified by chromatography on a column of silica gel, eluting with a cyclohexane/isopropyl ether (1/1 ratio) mixture.

23.73 g of product are obtained.

4.6.
(±)-6-Chloro-3-[2-[(1,2,3,4-tetrahydronaphthalen-1-yl) methylamino]ethyl]-4-[3-(trifluoromethyl) benzoyl]-3,4-dihydro-2H-1,4-benzoxazine (E)-2-butenedioate (1:1).

To a solution of 1.8 g (0.0044 mol) of (±)-6 -chloro-3-(2-chloroethyl)-4-[(3-trifluoromethyl)benzoyl]-3,4-dihydro-2H-1,4-benzoxazine in 13 ml of N,N-dimethylformamide, at room temperature, under an argon atmosphere and with magnetic stirring, are added 0.88 g (0.0044 mol) of N-methyl-1,2,3,4-tetrahydronaphthalene- 1-amine hydrochloride, 1.23 g (0.009 mol) of potassium carbonate and 0.74 g (0.0044 mol) of potassium iodide, and the mixture is heated at 120° C. for 1 h 30.

It is cooled and 50 ml of water are added to give a sticky product which is washed with water and dissolved in 50 ml of ethyl acetate, the solution is dried over magnesium sulphate and filtered, and the solvent is evaporated off under reduced pressure. 2.39 g of oily product are obtained, which product is purified by chromatography on a column of silica gel, eluting with a mixture of cyclohexane and ethyl acetate (in a ratio of 8/2).

1.62 g (0.003 mol) of base are obtained.

The fumarate is prepared by adding 0.35 g (0.003 mol) of fumaric acid to 15 ml of 2-propanol, the mixture is heated to reflux, the solvent is evaporated off under reduced pressure, the residue is taken up in diethyl ether, and the precipitate is isolated by filtration and recrystallized from 2-propanol. After drying under heat in the presence of phosphorus pentoxide, 0.3 g of fumarate is finally isolated. Melting point: 145°–146° C.

EXAMPLE 5

(Compound No. 38)

(±)-6-Chloro-3-[2-[(2,3-dihydro-1H-inden-2-yl) methylamino]ethyl]-4-[3-(trifluoromethyl) benzoyl]-3,4 -dihydro-2H-1,4-benzoxazine (E)-2-butenedioate (1:2).

5.1. (−)-6-Chloro-4-[(3-trifluoromethyl)benzoyl]-3,4 -dihydro-2H-1,4-benzoxazine-3-ethanol.

5.7 g (0.0148 mol) of (±)-6-chloro-4-[(3 -trifluoromethyl)benzoyl]-3,4-dihydro-2H-1,4 -benzoxazine-3-ethanol are dissolved in 60 ml of ethyl acetate, 570 mg of lipase from Mucor miehei at a concentration of 10% on resin (Lipozyme IM60™, Novo™) and 1.36 ml of vinyl acetate are added, and the mixture is stirred at room temperature, the reaction progress being monitored by HPLC on a chiral column, eluting with a mixture of hexane and 2-propanol (in a ratio of 95/5).

After reaction for 3 days, the degree of conversion is 52%, with an enantiomeric excess ee of alcohol greater than 98%. The mixture is filtered on kieselgel, rinsing the solid with 10 ml of ethyl acetate, the filtrate is concentrated under reduced pressure and the mixture of ester and of laevorotatory alcohol is separated by flash chromatography, using a 1/9 mixture of ethyl acetate and cyclohexane to elute the ester, followed by a 4/6 mixture to elute the alcohol.

2.5 g of laevorotatory alcohol and 3.0 g of ester are obtained.

Alcohol:$[\alpha]_D^{25}$=−48° (c=0.5; CHCl$_3$). ee=98.3%. Ester:ee=91%.

5.2. (+)-6-Chloro-3-[2-[(2,3-dihydro-1H-inden-2-yl) methylamino]ethyl]-4-[3-(trifluoromethyl) benzoyl]-3,4-dihydro-2H-1,4-benzoxazine (E)-2-butenedioate(1:2).

The process is performed under similar conditions to those described in the above examples, by treating (−) -6-chloro-4-[(3-trifluoromethyl)benzoyl]-3,4-dihydro-2H-1, 4-benzoxazine-3-ethanol with thionyl chloride in order to obtain 6-chloro-3-(2-chloroethyl)- 4-[(3-trifluoromethyl)benzoyl]-3,4-dihydro-2H-1,4 -benzoxazine (the optical rotation of which was not determined), then by reacting this compound with N-methyl-2,3-dihydro-1H-inden-2-amine, followed by treating the base with fumaric acid.

Melting point: 168°–169° C. $[\alpha]_D^{20}$=+16.2° (c=1; CH$_3$OH).

EXAMPLE 6

(Compound No. 39)

(−)-6-Chloro-3-[2-[(2,3-dihydro-1H-inden-2-yl) methylamino]ethyl]-4-[3-(trifluoromethyl) benzoyl]-3,4 -dihydro-2H-1,4-benzoxazine (E)-2-butenedioate (1:2).

6.1. (+)-6-Chloro-4-[(3-trifluoromethyl)benzoyl]-3,4-dihydro-2H-1,4-benzoxazine-3-ethanol.

The 3.0 g of ester obtained in Example 5.1 are dissolved in 14 ml of toluene, 70 ml of 0.3M phosphate buffer at pH=7.3 are added, the mixture is stirred vigorously at room temperature until an emulsion is formed, then 300 mg of free lipase from Mucor miehei (Biocatalyst™) are added and the reaction progress is monitored by HPLC on a chiral column as described in Example 5.1.

After reaction for 67 h, the degree of conversion is 28% and the pH is 6.95; it is adjusted to 7.5 with 4N sodium hydroxide, the mixture is warmed to 35° C. and the stirring is continued.

After reaction for 48 h, the degree of conversion is 67%; the pH is readjusted to 7.5, 300 mg of enzyme are added and the stirring is continued.

After reaction for 32 h, the degree of conversion is 82% and the enantiomeric excess of the alcohol is 98.1%. The mixture is then diluted with 100 ml of diethyl ether and filtered on kieselgel, the aqueous phase is extracted four times with 100 ml of diethyl ether, the organic phase is dried over magnesium sulphate, the solvent is evaporated off under reduced pressure and the residue is purified by chromatography as described in Example 5.1.

2.15 g of dextrorotatory alcohol and 0.49 g of ester are obtained.

Alcohol:$[\alpha]_D^{25}$=+51° (c=0.63; CHCl$_3$). ee=98.1%. Ester:ee=50%.

6.2. (−)-6-Chloro-3-[2-[(2,3-dihydro-1H-inden-2-yl) methylamino]ethyl]-4-[3-(trifluoromethyl) benzoyl]-3,4-dihydro-2H-1,4-benzoxazine (E)-2-butenedioate (1:2).

The process is performed under similar conditions to those described in the above examples, by treating (+)-6-chloro-4-[(3-trifluoromethyl)benzoyl]-3,4-dihydro-2H-1,4-benzoxazine-3-ethanol with thionyl chloride in order to obtain 6-chloro-3-(2-chloroethyl)- 4-[(3-trifluoromethyl)benzoyl]-3,4-dihydro-2H-1,4-benzoxazine (the optical rotation of which was not determined), then by reacting this compound with N-methyl-2,3-dihydro-1H-inden-2-amine, followed by treating the base with fumaric acid.
Melting point: 169°–170° C. $[\alpha]_D^{20}$=−16.9° (c=1; CH$_3$OH).

EXAMPLE 7

(Compound No. 36)

(±)-3-[2-[(2,3-Dihydro-1H-inden-2-yl)amino]ethyl]-6-nitro-4-[3-(trifluoromethyl)benzoyl]-3,4-dihydro-2H-1,4-benzoxazine (E)-2-butenedioate (1:2).

7.1. N-(2-Hydroxy-5-nitrophenyl)trifluoroacetamide.

A suspension of 18 g (0.116 mol) of 2-amino- 4-nitrophenol in 210 ml of diethyl ether is prepared, 16 ml of pyridine are added, the mixture is cooled in a bath of ice and ethanol and 24.5 g (0.116 mol) of trifluoroacetic anhydride are added dropwise.

The mixture is allowed to return to room temperature and stirring is continued overnight.

The mixture is poured into 200 ml of icewater and the organic phase is separated out and washed successively with 1N hydrochloric acid, with water, with saturated sodium hydrogen carbonate solution and with saturated sodium chloride solution. After drying over magnesium sulphate, 22.29 g of yellow solid are obtained, which product is used as it is in the following step.

7.2. Ethyl (±)-6-nitro-3,4-dihydro-2H-1,4-benzoxazine-3-acetate.

220 ml of ethanol are introduced into a 1 l three-necked flask, with magnetic stirring, cooled to 0° C., and 3 g (0.133 mol) of sodium are added slowly, in small portions, followed by successive dropwise addition of 22.29 g (0.088 mol) of N-(2-hydroxy-5-nitrophenyl)trifluoroacetamide and 22.65 g (0.088 mol) of 75% pure ethyl 4-bromo-2-butenoate, and the mixture is heated at reflux for 3 h.

The solvent is evaporated off and the residue is taken up in 53 ml of water and 21 ml of 1N sodium hydroxide and extracted with diethyl ether. The organic phase is washed with saturated sodium chloride solution, dried over magnesium sulphate and the solvent is evaporated off. An orange-red oil is obtained, which is purified by chromatography on a column of silica gel, eluting with a mixture of cyclohexane and ethyl acetate (in a ratio of 85/15).

9.25 g of product are obtained.

7.3. (±)-6-Nitro-3,4-dihydro-2H-1,4-benzoxazine-3-ethanol.

A mixture of 8.4 g (0.0317 mol) of ethyl (±)- 6-nitro-3,4-dihydro-2H-1,4-benzoxazine-3-acetate, 3 g (0.762 mol) of sodium borohydride and 133 ml of 1,1-dimethylethanol are heated to reflux, under an argon atmosphere, 26.6 ml of methanol are added dropwise and the heating is continued at reflux for 30 min.

The mixture is cooled in a bath of ice, 60 ml of water are added, the methanol and the 1,1-dimethylethanol are evaporated off and the aqueous mixture is extracted three times with 120 ml of ethyl acetate. The organic phase is washed twice with 80 ml of saturated sodium chloride solution, dried over magnesium sulphate and filtered, and the solvent is evaporated off under reduced pressure. 9.3 g of oily product are obtained, which product is purified by chromatography on a column of silica gel, eluting with a mixture of cyclohexane and ethyl acetate (in a ratio of 60/40).

5.2 g of product are obtained, which product crystallizes under cold conditions and which is used as it is in the following step.

7.4. (±)-6-Nitro-4-[3-(trifluoromethyl)benzoyl]-3, 4-dihydro-2H-1,4-benzoxazine-3-ethanol.

40 ml of dichloromethane, 5.16 g (0.023 mol) of (±)-6-nitro-3,4-dihydro-2H-1,4-benzoxazine-3-ethanol and 3.5 g (0.025 mol) of potassium carbonate are introduced into a 500 ml round-bottomed flask, 5.2 g (0.025 mol) of 3-(trifluoromethyl)benzoyl chloride dissolved in 40 ml of dichloromethane are added dropwise and the mixture is stirred at room temperature for 3.5 h.

22 ml of 1N sodium hydroxide are added, the dichloromethane is evaporated off and the aqueous residue is extracted with ethyl acetate. After washing and drying the organic phase, the solvent is evaporated off under reduced pressure and the residue is purified by chromatography on a column of silica gel, eluting with a mixture of cyclohexane and ethyl acetate (in a ratio of from 7/3 to 5/5). 5.4 g of pure product are obtained.

7.5. (±)-3-(2-Chloroethyl)-6-nitro-4-[3-(trifluoromethyl)benzoyl]-3, 4-dihydro-2H-1,4-benzoxazine.

To 5.37 g (0.0135 mol) of (±)-6-nitro-4-[3-(trifluoromethyl)benzoyl]-3,4-dihydro-2H-1,4 -benzoxazine-3-ethanol dissolved in 80 ml of dichloromethane are added dropwise 4.85 ml (0.0675 mol) of thionyl chloride and the mixture is stirred, while being kept warm in a bath of hot water, for 5 h 30.

The solvent is evaporated off, the residue is taken up in toluene, which is evaporated off, the residue is washed with diisopropyl ether and 21.74 g of product are obtained, which product is used as it is in the following step.

7.6. (±)-3-[2-[(2,3-Dihydro-1H-inden-2-yl) amino]ethyl]-6-nitro-4-[3-(trifluoromethyl) benzoyl]-3,4-dihydro-2H-1,4-benzoxazine (E)-2-butenedioate (1:2).

To a solution of 1.58 g (0.0038 mol) of (±)- 3-(2-chloroethyl)-6-nitro-4-[3-(trifluoromethyl)benzoyl]-3,4-dihydro-2H-1,4-benzoxazine in 15 ml of N,N-dimethylformamide, at room temperature, under an argon atmosphere and with magnetic stirring, are added 0.69 g (0.0038 mol) of N-methyl-2,3-dihydro-1H-inden-2-amine hydrochloride, 1.32 g (0.0095 mol) of potassium carbonate and 0.63 g (0.0038 mol) of potassium iodide, and the mixture is heated at 110° C. for 3 h 30.

It is cooled, 40 ml of water and 100 ml of diethyl ether are added, the phases are separated and the aqueous phase is extracted with twice 50 ml of diethyl ether. The organic phases are combined and washed with twice 50 ml of saturated sodium chloride solution, dried over magnesium sulphate and filtered, and the solvent is evaporated off. 2.5 g of oily product are obtained, which product is purified by chromatography on a column of silica gel, eluting with a mixture of dichloromethane and methanol (in a ratio of 98/2). 1.36 g of pure base are obtained in the form of a yellow oil. The fumarate is prepared by adding one equivalent of fumaric acid to the base in solution in hot 2-propanol, and it is isolated and recrystallized from methanol.

0.90 g of fumarate is finally isolated. Melting point: 176°–178° C.

The table which follows illustrates the chemical structures and the physical properties of a few of the compounds according to the invention. In the "Salt" column, "—" denotes a compound in the form of a base, "ox." denotes an oxalate, or ethanedioate, and "fum." denotes a fumarate, or (E)-2-butenedioate; the ratio indicated in parentheses is the acid:base molar ratio.

TABLE (Structure I: substituted benzene with $R_1$, linked to N bearing a 3-(trifluoromethyl)benzoyl group, with a side chain $-CH(CH_2OAr)CH_2CH_2NR_3R_4$)

| No. | $R_1$ | $R_3$ | $R_4$ | Salt | m.p. (°C.) | Observations |
|---|---|---|---|---|---|---|
| 1 | H | 2-(1H-indol-3-yl)ethyl | H | fum. (1:1) | 211–212 | — |
| 2 | 6-F | 2-(1H-indol-3-yl)ethyl | H | fum. (1:1) | 233–234 | — |
| 3 | 6-Cl | 2-(1H-indol-3-yl)ethyl | H | ox. (1, 3:1) | 153–155 | — |
| 4 | 6-CH$_3$ | 2-(1H-indol-3-yl)ethyl | H | ox. (1, 1:1) | 159–161 | — |
| 5 | 6-OCH$_3$ | 2-(1H-indol-3-yl)ethyl | H | fum. (1:1) | 235–237 | — |
| 6 | H | 2-(1H-indol-3-yl)ethyl | H | fum. (0, 5:1) | 227–228 | — |

TABLE-continued
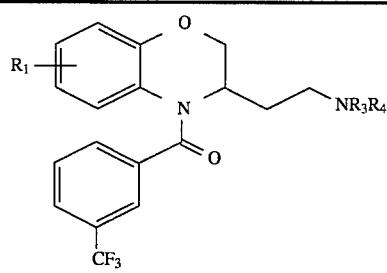
| No. | R₁ | R₃ | R₄ | Salt | m.p. (°C.) | Observations |
|---|---|---|---|---|---|---|
| 7 | 6-F | | 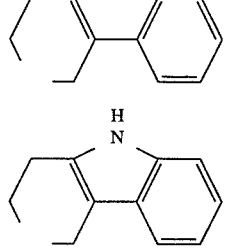 | fum. (0,6:1) | 234–235 | — |
| 8 | 6-Cl | | 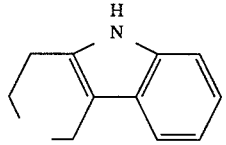 | ox. (1:1) | 145–147 | — |
| 9 | 6-CH₃ | | 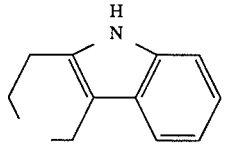 | ox. (0, 9:1) | 147–149 | — |
| 10 | 6-OCH₃ | | 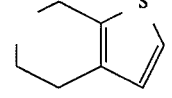 | fum. (0, 5:1) | 251–253 | — |
| 11 | H | | 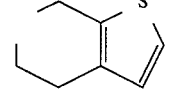 | fum. (1, 25:1) | 169–170 | — |
| 12 | 6-F | | 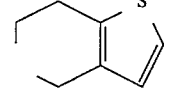 | fum. (1:1) | 181–182 | — |
| 13 | H | | 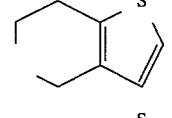 | fum. (1:1) | 185–186 | — |
| 14 | 6-F | | 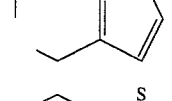 | fum. (1:1) | 208–209 | — |
| 15 | 6-Cl | | 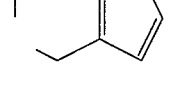 | ox. (1:1) | 197–199 | — |
| 16 | 6-CH₃ | | | ox. (1:1) | 199–201 | — |

TABLE-continued (I)

[Structure: benzoxazine core with R₁ on aromatic ring, N-benzoyl substituent bearing 3-CF₃, and side chain -CH₂CH₂-NR₃R₄]

| No. | R₁ | R₃ | R₄ | Salt | m.p. (°C.) | Observations |
|-----|------|------------|----------------|-----------|-----------|-----------------------|
| 17 | H | | 2,3-diethylphenyl | fum. (1:1) | 199–200 | — |
| 18 | H | CH₃ | indan-2-yl | ox. (1, 5:1) | 154–155 | — |
| 19 | 6-F | CH₃ | indan-2-yl | ox. (1:1) | 153–154 | — |
| 20 | 6-Cl | CH₃ | indan-2-yl | ox. (0, 9:1) | 173–175 | — |
| 21 | 6-Cl | CH₂CH₂CH₃ | indan-2-yl | ox. (1:1) | 127–129 | — |
| 22 | 6-CH₃ | CH₃ | indan-2-yl | ox. (1:1) | 158–160 | — |
| 23 | 6-CH₃ | CH₂CH₂CH₃ | indan-2-yl | ox. (1:1) | 89–91 | — |
| 24 | 6-OCH₃ | CH₃ | indan-2-yl | ox. (1:1) | 185–187 | — |
| 25 | 6-OCH₃ | CH₂CH₂CH₃ | indan-2-yl | ox. (1:1) | 139–141 | — |
| 26 | H | H | indan-2-yl | ox. (1:1) | 193–194 | — |
| 27 | 6-Cl | H | indan-2-yl | fum. (1:1) | 206–207 | — |
| 28 | H | CH₃ | indan-1-yl | ox. (1:1) | 152–153 | only 1 diastereoisomer |

TABLE-continued

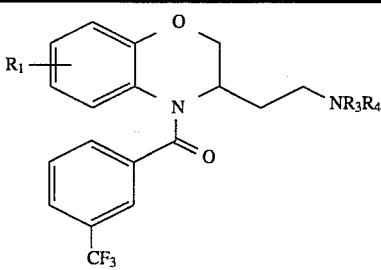
(I)

| No. | R₁ | R₃ | R₄ | Salt | m.p. (°C.) | Observations |
|---|---|---|---|---|---|---|
| 29 | 6-Cl | CH₃ | 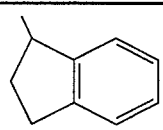 | fum. (1:1) | 188–189 | 90:10 mixture of diastereoisomers |
| 30 | 6-Cl | CH₃ | 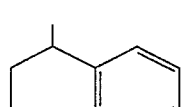 | fum. (1:1) | 145–146 | 65:35 mixture of diastereoisomers |
| 31 | H | CH₃ | 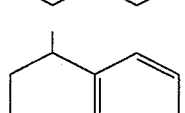 | ox. (1:1) | 142–143 | 54:46 mixture of diastereoisomers |
| 32 | 7-CH₃ | CH₃ | 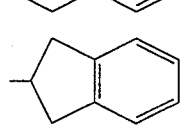 | fum. (0.5:1) | 163–165 | — |
| 33 | 7-CH₃ | CH₃ | 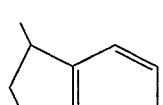 | fum. (1:1) | 165–167 | 60:40 mixture of diastereoisomers |
| 34 | 7-CH₃ | H | 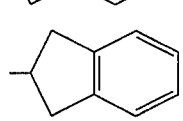 | ox. (1.1:1) | 208–210 | — |
| 35 | 6-NO₂ | CH₃ | 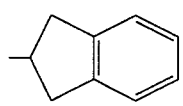 | ox. (1.1:1) | 194–196 | — |
| 36 | 6-NO₂ | H | 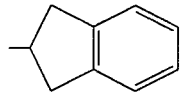 | fum. (0.5:1) | 176–178 | — |
| 37 | 6-NO₂ | CH₃ | 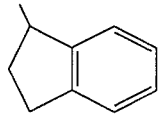 | fum. (1:1) — | 178–180 138–140 | diastereoisomer A diastereoisomer B |
| 38 | 6-Cl | CH₃ | 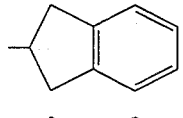 | fum. (0.5:1) | 168–169 $[\alpha]_D^{20} = +16.2°$ (c = 1; CH₃OH) | dextrorotatory enantiomer |
| 39 | 6-Cl | CH₃ | 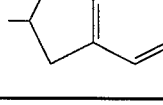 | fum. (0.5:1) | 169–170 $[\alpha]_D^{20} = -16.9°$ (c = 1; CH₃OH) | laevorotatory enantiomer |

The compounds of the invention underwent various trials which demonstrated their advantage as therapeutic substances.

Thus, they were subjected to the global cerebral ischaemia test in mice. The ischaemia is due to a cardiac arrest induced by a rapid intravenous injection of magnesium chloride. In this test, the "survival time" is measured, that is to say the interval between the moment of the injection of magnesium chloride and the final observable respiratory movement of each mouse. This final movement is considered as the ultimate indication of central nervous system functioning.

Respiratory arrest appears approximately 19 seconds after the injection of magnesium chloride.

Male mice (Swiss OF1 IFFA CREDO) are studied in groups of 10. They are given food and drink ad libitum before the tests. The survival time is measured 10 minutes after intraperitoneal administration of the compounds of the invention. The results are given in the form of the difference between the survival time measured in a group of 10 mice which received the compound and the survival time measured in a group of 10 mice which received only the vehicle liquid. The ratios between the changes in the survival time and the dosage of the compound are recorded graphically as a semilogarithmic curve.

This curve makes it possible to calculate the "3 second effective dose" ($ED_3$.), that is to say the dose (in mg/kg) which produces a 3-second increase in the survival time relative to the control group of 10 untreated mice.

A 3-second increase in the survival time is both statistically significant and reproducible.

The $ED_3$. of the compounds of the invention range from 0.1 to 30 mg/kg via the intraperitoneal route.

The compounds of the invention were also the subject of a study of the potential-dependent ("voltage-dependent") barium currents by the so-called "patch-clamp" technique.

The barium currents flowing through the potential-dependent calcium channels are measured on a preparation of new-born rat (Sprague-Dawley) cortex cells in culture (cultured for 6 to 10 days); in the case of these cells, these are composite currents which involve the L, N and P channels, as described in *Soc. Neurosci. Abstr.* (1989) 15 823.

The measuring chambers, 800 μl in volume, containing the cortex cells, are placed on the stage of an olympus IMT-2™ inverted microscope and the cells are observed at a magnification of 400×. The chambers are perfused continuously (4 to 5 ml/min) using a solution distributor device having 9 inputs (dead volume <50 μl), the sole outlet of which, consisting of a polyethylene tube with a 500 μm opening, is placed less than 3 mm away from the cell studied. This device has the advantage of allowing a rapid change of solution on the cells studied.

The patch-clamp method used is described in *Pfluegers Archives* (1981) 391 85–100. An Axopatch-1D™ amplifier connected to an AT 386-33 MHz type computer, using PCLAMP™ software from Axon Instruments™, is used for stimulation of the cells, acquisition of the data and analysis of the results. In order to record the barium currents, borosilicate glass pipettes are brought close to the cells by means of a Narishige WR 60™ hydraulic micromanipulator. The tip of the pipettes is filled with the reference intracellular solution, the composition (in mM) of which is as follows: CsCl (140), $CaCl_2$ (1), $Na_2ATP$ (4), EGTA (11; pCa=8), Hepes (10), Tris-OH (pH=7.2).

Once the so-called "whole cell" configuration is obtained, the cell is perfused with a so-called TEA-Barium solution, the composition (in mM) of which is as follows: TEA-Cl (144), $BaCl_2$ (5), $MgCl_2$ (2), CsCl (3), glucose (10), Hepes (10), Tris-OH (pH=7.4).

This solution makes it possible to measure the calcium current (similar to the barium current flowing through the potential-dependent calcium channels) while at the same time being independent of the sodium and potassium currents.

The global potential-dependent barium current is obtained by application of a depolarizing potential step with a duration of 250 ms, taking the membrane potential from −80 mV to 0 mV. The stimulation frequency is 0.25 Hz.

The compounds of the invention are dissolved in the TEA-barium medium and are applied once the amplitude of the barium current has stabilized. After obtaining a stable inhibitory effect, the cell is again perfused with the control TEA-barium solution in order to observe reversal of the effect.

The strength of the effect obtained is compared to that of a 100 μM cadmium solution. Inhibition of the potential-dependent barium current varies as a function of the doses of compounds studied and, for the most active compounds, is of the order of 40% at a concentration of 1 μM and of 90% at a concentration of 10 μM.

The results of the tests carried out on the compounds of the invention show that, in vitro, they have neuronal calcium antagonist properties and, in vivo, they have neuroprotective and anti-ischaemic properties.

These results suggest that the compounds may be used for the treatment and prevention of cerebral disorders such as those following, for example, an ischaemic attack, a cardiac or respiratory arrest, a cerebral embolism or thrombosis, for the treatment of cerebral senility, dementia following multiple infarctions, senile dementia, for example Alzheimer's disease or Pick's disease, for the treatment of olivopontocerebellar atrophy and other neurodegenerative diseases such as Huntington's chorea and amyotrophic lateral sclerosis, for the treatment of cranial or spinal trauma, for the prevention of neuronal damage following convulsive states, for the treatment of certain cancers, for the treatment of neurological damage caused by AIDS, and for the prevention and treatment of diabetic retinopathies, degeneration of the optic nerve and retinopathies associated with glaucoma, and in general for the treatment of any pathology associated with dysfunction of the neuronal calcium homeostasis.

To this end, the compounds may be provided in all pharmaceutical forms adapted for enteral or parenteral administration, in combination with suitable excipients, for example in the form of tablets, sugar-coated tablets, gelatin capsules, wafer capsules, suppositories, or drinkable or injectable solutions or suspensions, which are dosed to allow a daily administration of, say, 1 to 1000 mg of active substance.

We claim:

1. Compound of the formula

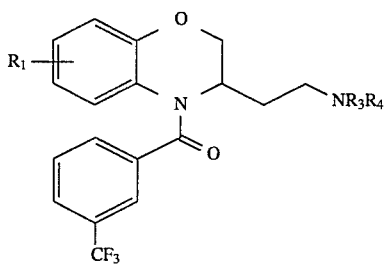 (I)

wherein
 $R_1$ represents a hydrogen, fluorine or chlorine atom or a methyl, $C_1$–$C_3$ alkoxy or nitro group;
 $R_3$ represents a hydrogen atom or a $C_1$–$C_3$ alkyl group;
 $R_4$ represents a 2,3-dihydro-1H-inden-2-yl group, a 2,3-dihydro-1H-inden-1-yl group or a 1,2,3,4-tetrahydronaphthalen-1-yl group;
or alternatively
 $R_3$ and $R_4$ together complete, with the nitrogen atom to which they are attached, a 1,2,3,4-tetrahydro-9H-pyrido[3,4-b]indol-2-yl group, a 1,2,3,4-tetrahydro-9H-pyrido[4,3-b]indol-3-yl group, a 4,5,6,7-tetrahydrothieno[2,3-c]pyrid-6-yl group, a 4,5,6,7-tetrahydrothieno[3,2-c]pyrid-6-yl group or a 2,3-dihydro-1H-isoindol-2-yl group, the respective formulae of which are as follows:

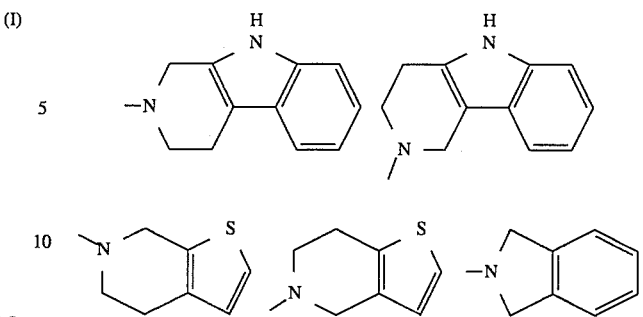

in the form of a base or of an addition salt with an acid; and either in the form of a pure optical isomer or a mixture of optical isomers.

2. Compound according to claim 1, wherein $R_1$ represents a fluorine or chlorine atom or a methyl or methoxy group, $R_3$ represents a hydrogen atom or a $C_1$–$C_3$ alkyl group and $R_4$ represents a 2,3-dihydro-1H-inden-2-yl group, a 2,3-dihydro-1H-inden-1-yl group or a 1,2,3,4-tetrahydronaphthalen-1-yl group.

3. A pharmaceutical composition, comprising a compound as claimed in claim 1 and an excipient.

* * * * *